United States Patent [19]

Delprato

[11] Patent Number: 4,849,327
[45] Date of Patent: Jul. 18, 1989

[54] SILVER HALIDE LIGHT-SENSITIVE MATERIAL COMPRISING BENZO-BIS-THIAZOLE QUATERNARY SALTS AS ANTIFOGGING AGENTS

[75] Inventor: Ivano Delprato, Savona, Italy

[73] Assignee: Minnesota Mining and Manufacturing Company, St. Paul, Minn.

[21] Appl. No.: 198,989

[22] Filed: May 26, 1988

[30] Foreign Application Priority Data

Jun. 2, 1987 [IT] Italy ................................ 20751 A/87

[51] Int. Cl.⁴ ........................... G03C 1/34; G03C 7/32
[52] U.S. Cl. ..................................... 430/551; 430/570; 430/611; 430/614; 548/151
[58] Field of Search ............... 430/551, 570, 611, 614; 548/151

[56] References Cited

U.S. PATENT DOCUMENTS

| | | | |
|---|---|---|---|
| 2,131,038 | 9/1938 | Brooker et al. | 95/7 |
| 3,954,478 | 5/1976 | Arai et al. | 96/100 |
| 4,237,214 | 12/1980 | Mifune et al. | 430/441 |

*Primary Examiner*—Richard L. Schilling
*Assistant Examiner*—Janet C. Baxter
*Attorney, Agent, or Firm*—Donald M. Sell; Walter N. Kirn; Mark A. Litman

[57] ABSTRACT

Benzo-bis-thiazole quaternary salts having attached to at least one quaternary nitrogen atom thereof an alkenyl group carrying a double bond in the $\beta$-position and their use as antifogging agents in silver halide light-sensitive materials.

12 Claims, No Drawings

SILVER HALIDE LIGHT-SENSITIVE MATERIAL COMPRISING BENZO-BIS-THIAZOLE QUATERNARY SALTS AS ANTIFOGGING AGENTS

FIELD OF THE INVENTION

The present invention relates to benzo-bis-thiazole quaternary salts having linked to at least one quaternary nitrogen thereof an alkenyl group having a double bond in the β-position and to their use as antifogging agents in a light-sensitive material comprising a light sensitive silver halide emulsion.

BACKGROUND OF THE ART

During the processing of a photographic element containing an imagewise exposed silver halide emulsion layer, reduced silver can be formed as a function of exposure. At the same time, at least a low level formation of reduced silver also occurs independently of imagewise exposure.

The term "fog" is herein employed to indicate the undesired formation of developed silver—or of developed dye in the case of color photography—in non-exposed areas.

Such fog is related to the fact, known to the man skilled in the art, that sensitivity centers of the silver halide grains may be rendered developable in the absence of light exposure. Fog generally increases with emulsion sensitivity, thus impairing the quality of the obtained photographic material.

In color photography the problem may be particularly serious, since a colored fog is generally more visible than a black and white fog.

The problem of reduction of fog formation may be reduced with substances which have the property of decreasing only fog without significantly reducing sensitivity. Such substances are reactivity associated with the photographic emulsion by introducing them into the layer containing said emulsion.

To eliminate this problem, various materials have been introduced into the photographic silver halide emulsion. Antifog agents have been described since the beginning of photography, as one can read for instance in "Stabilization of Photographic Silver Halide Emulsion", by E. J. Birr (Focal Press).

The most common materials to prevent fog formation are listed in Research Disclosure, Vol. 176, December 1978, No. 17643. Brooker et al., in U.S. Pat. No. 2,131,038, disclose thiazolium salts, including a simple cyanine dye, as useful antifogging agents. Mifune et al., U.S. Pat. No. 4,237,214, disclose benzothiazolium salts having quaternary substituents that can contain a carbamoyl or a sulfamoyl group as antifoggants. It has been generally recognized in the art that a particulary useful class of antifogging agents is represented by alkyl (including allyl) substituted thiazolium, benzothiazolium, selenazolium and benzoselenazolium salts. On the other hand, quaternary oxazolium salts are not generally known to be useful as antifogging agents. Arai et al., U.S. Pat. No. 3,954,478, disclose a silver halide emulsion containing alkenylbenzothiazolium salts as latent image stabilizers.

Problems are sometimes encountered with the use of antifogging agents. These problems relate to reduction of sensitivity caused by antifoggants when used in amounts effective to inhibit fogging. Therefore there is the need to provide compounds that inhibit fog formation during manufacture and storage of silver halide photographic materials, which do not cause a marked reduction in sensitivity.

SUMMARY OF THE INVENTION

Benzo-bis-thiazole quaternary salts having attached to at least one quaternary nitrogen thereof an alkenyl group having a double bond in the β-position associated with silver halide emulsion layers of light-sensitive silver halide photographic materials inhibit fog formation without causing a significant reduction in sensitivity.

DETAILED DESCRIPTION OF THE INVENTION

In one aspect, the present invention refers to a silver halide light-sensitive material comprising a silver halide light-sensitive emulsion associated with a benzo-bis-thiazole quaternary salt antifogging agent attached to at least one quaternary nitrogen an alkenyl group having a double bond in the β-position.

In particular, the present invention refers to a silver halide light sensitive material comprising a silver halide light-sensitive emulsion associated with a benzo-bis-thiazole quaternary salt as antifogging agent represented by the general formula (I):

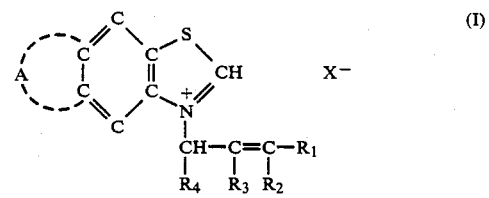

wherein $R_1$, $R_2$, $R_3$, $R_4$ each represents a hydrogen atom or a lower alkyl group, A represents the atoms necessary to complete a benzo-bis-thiazole nucleus and $X^-$ is an anion.

More particularly, the present invention refers to a silver halide light-sensitive material comprising a silver halide light-sensitive emulsion associated with a benzo-bis-thiazole quaternary salt antifogging agent represented by the following general formula (II):

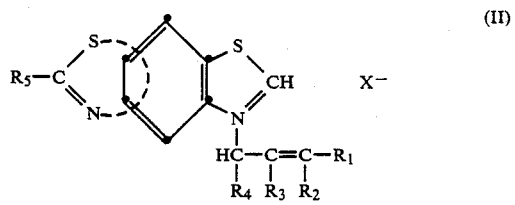

wherein $R_5$ is hydrogen atom or a lower alkyl group and $R_1$, $R_2$, $R_3$, $R_4$ and $X^-$ are the same as above.

In another aspect, the present invention relates to benzo-bis-thiazole quaternary salts having attached to at least one quaternary nitrogen thereof an alkenyl group having a double bond in the β-position as described above, with particular reference to formulas (I) and (II).

In the previous formulas (I) and (II) the non-quaternized thiazole group may be fused to the benzene ring by linking the nitrogen atom and the sulphur atom to the positions 3, 4, 5, or 6 of the benzene ring. By this way, the nitrogen atom may be linked to the 3-position and the sulphur atom to the 4-position of the benzene ring or viceversa (thus obtaining a benzo(1,2-d:4,3-d')-bis-thiazole quaternary salt and a benzo-(1,2-d:3,4-d')-bisthiazole quaternary salt, respectively), or the nitrogen atom may be linked to the 4-position and the sulphur atom to the 5-position of the benzene ring or viceversa (thus obtaining a benzo-(1,2-d:5,4-d')-bisthiazole quaternary salt and a benzo-(1,2-d:4,5-d')-bisthiazole quaternary salt, respectively) or the nitrogen atom may be linked to the 5-position and the sulphur atom to the 6-position of the benzene ring or viceversa (thus obtaining a benzo-(1,2-d:6,5-d')-bisthiazole quaternary salt and a benzo-(1,2-d:5,6-d')-bisthiazole quaternary salt, respectively).

Lower alkyl groups represented by $R_1$, $R_2$, $R_3$ and $R_4$ have from 1 to 5 carbon atoms; suitable lower alkyl groups are a methyl group, an ethyl group, a propyl group, an iso-propyl group, a butyl group, an isobutyl group, a tertiary-butyl group, a normal pentyl group or a tertiary amyl group. The total carbon atoms of the lower alkyl groups represented by $R_1$, $R_2$, $R_3$ and $R_4$, when more than one group is present, is such as not to negatively affect the antifogging properties of the benzo-bis-thiazole quaternary salts according to this invention. The lower alkyl groups represented by $R_1$, $R_2$, $R_3$ and $R_4$ may have up to a maximum of 20 carbon atoms. Preferably, said total number of carbon atoms of $R_1$, $R_2$, $R_3$ and $R_4$ is less than 15, more preferably less than 5.

The lower alkyl group represented by $R_5$ has from 1 to 5 carbon atoms; suitable lower alkyl groups are a methyl, ethyl, propyl, iso-propyl, butyl, iso-butyl, tertiary butyl, normal pentyl or tertiary amyl group, preferably a methyl group.

$X^-$ of formulas (I) and (II) above represents an acid anion (e.g. chloride, bromide, iodide, thiocyanate, methylsulfate, ethylsulfate, perchlorate, p-toluenesulfonate ions or other well-known photographically inert or harmless anions).

Typical examples of the benzo-bis-thiazole quaternary salts according to the present invention include the following:

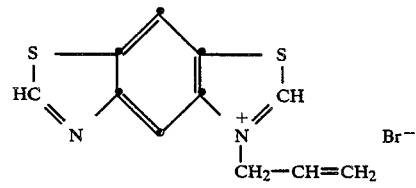

(1)

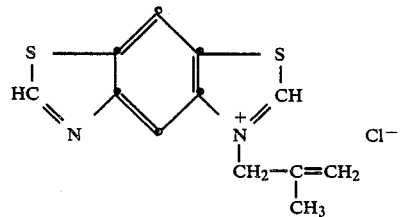

(2)

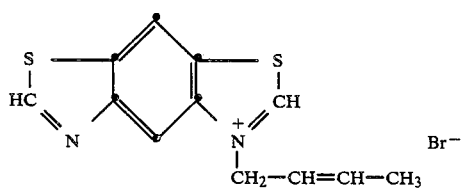

(3)

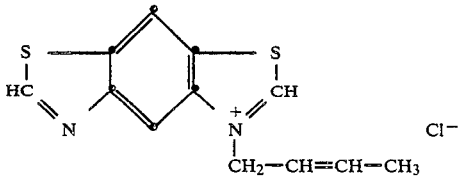

(4)

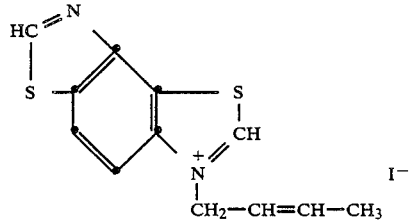

(5)

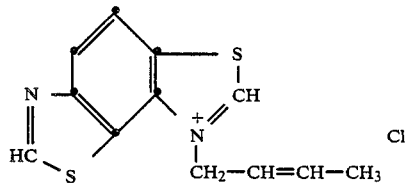

(6)

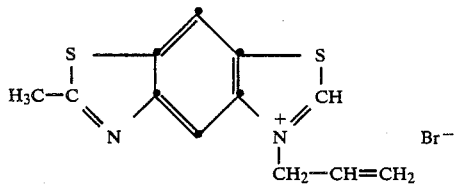

(7)

The benzo-bis-thiazole quaternary salts antifogging agents according to the present invention may be incorporated in any layer of the silver halide photographic material, such as in a silver halide emulsion layer or a hydrophilic colloidal layer in water permeable association with a silver halide emulsion layer. Preferably, said antifogging agents are used by incorporation in the silver halide emulsion layer.

The benzo-bis-thiazole quaternary salts antifogging agents according to the present invention may be added during each step of the preparation of the photographic material. They may be added during the emulsion making, the physical ripening, before or after the chemical ripening and before or during the coating process, as known in the art.

The most useful amount of the antifogging agents of the present invention varies correspondingly with various factors, such as the silver halide composition, the nature of the other components of the emulsion, the use of the photographic element, and the like. However, useful amounts are generally in the range from about 0.01 to about 10 millimoles per mole of silver and preferably from about 0.1 to about 5 millimoles per mole of silver.

The silver halide emulsions used in the present invention can be any of the silver halide emulsions known in the art, such as silver chloride, silver bromide, silver bromo-chloride, silver chloro-iodide, silver bromo-iodide, silver chloro-bromo-iodide emulsions and mixtures thereof. The emulsions can be composed of coarse, medium and fine grains and can be monodispersed or polydispersed. The silver halide grains may be those having a regular crystal form, such as a cube or an octahedron, or those having an irregular crystal form, such as a sphere or tablet, etc., or may be those having a composite crystal form. They may be composed of a mixture of grains having different crystal forms. Their size can be varied on a wide range, but in general average grain sizes from 0.1 to 4 μm are suitable.

The silver halide emulsions used in the present invention may be obtained according to any of the known acid, neutral and ammoniacal method using conventional precipitation methods such as a single or twin jet method.

Further, the silver halide emulsions may be chemically sensitized with a sulfur sensitizer, such as allylthiocarbamide, thiourea, cystine, etc.; an active or inert selenium sensitizer; a reducing sensitizer such as stannous salt, a polyamine, etc.; a noble metal sensitizer, such as gold sensitizer, more specifically potassium aurithiocyanate, potassium chloroaurate, etc.; or a sensitizer of a water soluble salt such as for instance of ruthenium, rhodium, iridium and the like, more specifically, ammonium chloropalladate, potassium chloroplatinate and sodium chloropalladite, etc.; each being employed either singly or in a suitable combination.

The antifogging agents of the present invention are preferably incorporated in the silver halide emulsion. They can be added to the silver halide emulsion at any point after the formation of the silver halide grains, preferably after chemical and spectral sensitization, but before coating of the emulsion on the support, so that they can interact with the grains prior to exposure.

Furthermore, the above silver halide emulsions may contain various known additives for photography. For example, there may be employed additives for photography as disclosed in Research Disclosure, 17643, December 1978.

Further, the silver halides may be optically sensitized to a desired wavelength region. The method for spectral sensitization of the present invention is not particularly limited. For example, optical sensitization may be possible by using an optical sensitizer, including a cyanine dye, a merocyanine dye, complex cyanine and merocyanine dyes, oxonol dyes, hemioxonol dyes, styryl dyes and streptocyanine dyes, either alone or in combination. Particularly useful optical sensitizers are the dyes of the benzoxazole, benzimidazole and benzothiazole carbocyanine type.

The above emulsions may also contain various additives conveniently used depending to their purpose. These additives include, for example, stabilizers or antifoggants such as azaindenes, triazoles, tetrazoles, imidazolium salts, polyhydroxy compounds and others; film hardeners such as of aldehyde type, aziridine type, isoxazole type, vinylsulfone type, acryloyl type, triazine type, etc.; developing promoters such as benzyl alcohol, polyoxyethylene type compounds, etc.; image stablizers such as chromane type, cumarane type, bisphenol type, etc.; and lubricants such as wax, glycerides of higher fatty acids, higher alcohol esters of higher fatty acids, etc. Also, coating aids, modifiers of the permeability in the processing liquids, defoaming agents, antistatic agents and matting agents may be used. As hydrophilic colloids to be used in the emulsion according to the present invention, not only gelatin but also gelatin derivatives, polymer grafts of gelatin, synthetic hydrophilic macromolecular substances and natural hydrophilic macromolecular substances other than gelatin may also be available either as a single species or in a mixture. Also, synthetic latexes may be added to gelatin to improve the film properties such as copolymers of acrylic acid esters, vinyl esters, etc. with other monomers having ethylenic groups.

As the support for the light-sensitive element, there may be used, for example, baryta paper, polyethylene-coated paper, polypropylene synthetic paper, cellulose acetate, polystyrene, a polyester film such as polyethyleneterephthalate, etc. These supports may be chosen depending on the purpose of use of the light-sensitive silver halide photographic material. The supports may be provided with a subbing layer, if necessary.

The photographic emulsions of the present invention can be used for black-and-white light-sensitive negative elements, light-sensitive positive elements, X-ray elements, lithographic elements, black-and-white and color light-sensitive elements for diffusion transfer processes and light-sensitive elements which contain oil-soluble or water-soluble color couplers.

Preferably, the silver halide emulsions according to the present invention can be designed for multicolor elements comprising dye image forming units sensitive to each of the three primary regions (blue, green and red) of the visible spectrum. Each unit can be formed by a single emulsion layer or multiple emulsion layers sensitive to the same spectral region.

More preferably, the silver halide emulsions according to the present invention can be designed for a multicolor element comprising a support bearing at least one blue-sensitive silver halide emulsion layer and preferably two blue-sensitive silver halide emulsion layers of different sensitivity associated with yellow dye forming couplers, at least one green sensitive silver halide emulsion layer and preferably two green-sensitive silver halide emulsion layers of different sensitivity associated with magenta dye forming couplers, and at least one red-sensitive silver halide emulsion layer and preferably at least two red-sensitive silver halide emulsion layers of different sensitivity associated with cyan dye forming couplers, wherein at least one silver halide emulsion layer comprises an antifogging agent of the present invention.

Said yellow, magenta and cyan dye forming couplers may be incorporated in any layer of the silver halide photographic material, such as in a silver halide emulsion layer or a hydrophilic colloidal layer in water permeable association with a silver halide emulsion layer. Preferably, said dye forming couplers are used by incorporation in the silver halide emulsion layer.

As yellow couplers, there may be employed, for example, the known open-chain ketomethylene type couplers. Among them, benzoylacetanilide type and pivaloylacetanilide type compounds are useful.

As magenta couplers, there may be employed, for example, pyrazolone type compounds, pyrazolotriazole type compounds, indazolone type compounds, cyanoacetyl type compounds. As cyan couplers, for example, phenol type compounds and naphthol type compounds are useful.

The elements of the present invention can contain additional layers of common use in photographic elements such as protective layers, intermediate layers, filter layers, antihalation layers and the like.

The benzo-bis-thiazole quaternary salts of the present invention can be prepared by reacting a benzo-bis-thiazole with an alkenyl derivative as known in the art with reference to quaternization procedures of thiazole compounds. The preparation of compound (1) is described hereinbelow, all other compounds described therein being prepared by following the same procedures.

PREPARATION OF BENZO(1,2-d:5,4-d')-BIS-THIAZOLE N-ALLYLBROMIDE (COMPOUND 1)

(a) Synthesis of 1,3-dichloro-4,6-dinitrobenzene (compound (A)

Ml. 11.3 of fuming nitric acid (0.275 mole) in 96% $H_2SO_4$ (50 ml) was dropwise added under stirring at room temperature to 48 g of 1,3-dichloro-4-nitrobenzene (0.25 mole) in 96% $H_2SO_4$ (350 ml). The mixture was stirred for two hours, then poured into crushed ice. The separated solid was washed with cold water to neutrality, dried under vacuum and crystallized from ethanol (170 ml) to give the dinitro compound (A), 45.5 g, yield 76.8%, as yellow prisms.

Analysis. $C_6H_2Cl_2N_2O_4$ requires C 30.41; H 0.85; N 11.82; found C 30.26; H 0.80; N 11.73.

(b) Synthesis of benzo(1,2-d;5,4-d')bis-thiazole (compound (B)

Step 1.

5.0 g of compound (A) (0.211 mole) in hot ethanol (100 ml) was poured into 7.8 g of NaSH (0.105 mole) in water (100 ml) under a nitrogen stream. The mixture was stirred for 3 hours, then diluited with water (400 ml) and acidified with 37% HCl. The separated solid was filtered, washed with water and dried to give 4.7 g of the crude derivative.

Step 2.

11.6 g of the so obtained compound were added under a nitrogen stream with stirring to 6.0 g of NaOH (0.150 mole) in water (ml 200). 60.9 g of $Na_2S_2O_4$ (0.350 mole) were added portionwise to the above stirred mixture. The temperature raised to 50° C. and stirring was maintained for 1 hour. 350 ml of HCOOH (99%) were then added and the resulting mixture was refluxed for 3 hours. The hot mixture was filtered, cooled and made basic with 30% NaOH. The separated solid was filtered, washed with water and dried to give the benzo-bis-thiazole (g 5.60, yield 58%).

Analysis. $C_8H_4N_2S_2$ requires C 49.98; H 2.10; N 14.57; S 33.36; found C 49.86; H 2.06; N 14.52; S 33.05.

(c) Synthesis of benzo(1,2-d:5,4-d')-bis-thiazole N-allylbromide (compound 1)

6.3 g (0.033 mole) of benzo(1,2-d:5,4-d')-bis-thiazole (compound (B)) were heated in a scaled steel tube at 110° C. for 3 hours with 5.5 g (0.65 mole) of allylbromide. The separated solid was washed with ethylacetate and dried under vacuum at 60° C. to give 9.3 g of compound 1 (Yield 91%).

| Analysis: | found | calculated |
|---|---|---|
| N | 8.81 | 8.94 |
| C | 41.48 | 42.18 |
| H | 2.79 | 2.90 |
| S | 19.90 | 20.47 |
| Br | 25.28 | 25.51 |

The following examples further illustrate the invention.

EXAMPLE 1

A 2% methanol solution of compound 1 was prepared to be added to a blend of low and medium speed emulsions in such a quantity to get a molar ratio of 0.5 millimoles of Compound 1 to 1 mole of silver. Said blend was obtained with 60% (by weight) of a slow speed AgBrI emulsion having 97.5% mol.Br$^-$, 2.5% mol.I$^-$, an average grain size diameter of 0.31 μm and a silver/gelatin ratio of 1.12, and with 40% of a medium speed AgBrICl emulsion having 87.7% mol Br$^-$, 7.17% mol I$^-$, 5.31% mol Cl$^-$, an average grain size diameter of 0.43 μm and a silver/gel ratio of 1.26. The emulsion was then held for 20 minutes at 36° C. under stirring, chemically sensitized with gold and thiosulfate, stabilized with 4-methyl-6-hydroxytetrazaindene and optically sensitized with 1-ethyl-1'-(3-sulfopropyl-pyrrolino-2,2'-carbocyanine) hydroxide. This emulsion was added with Compound 1, in the above described quantity, and with α-pivaloyl-α-(3-morpholino-1,2,4-triazol-1-yl)-2-chloro-5-(n-hexadecanesulfonamido)-acetanilide coupler, dispersed with the aid of a high boiling solvent to give a silver to coupler molar ratio of 3.43, before coating on a colloidal silver yellow filter above a cellulose triacetate base at a coverage of 1.0 g silver per square meter (film 1).

A similar film was obtained in the same manner of the previuos film 1, except that a 2% methanol solution of compound 1 was added to a blend of low and medium speed emulsions in such a quantity to get a molar ratio of 1 millimole of Compound 1 to 1 mole of silver (film 2).

A similar film was obtained in the same manner of the previuos film 1, except that a 2% methanol solution of compound 1 was added to a blend of low and medium speed emulsions in such a quantity to get a molar ratio of 2 millimole of Compound 1 to 1 mole of silver (film 3).

A further photographic element as control film was prepared and coated as above, except that no compound was specifically added to the emulsion (film 4).

Each film had a gelatin protective layer coated on top, containing the 1,3-dichloro-5-hydroxytriazine hardener.

A sample (S1) of each film was exposed to a light source having a color temperature of 5500° K. through a continuous wedge of gradient 0.30 and then stored for 30 days in freezer.

Another sample (S2) of each film was exposed in the same way and then stored for 30 days at 24° C. 50% RH.

A third sample (S3) of each film was stored in freezer for 30 days before exposure; a fourth sample (S4) of each film was stored at 24° C. 50% RH for 30 days before exposure.

After 30 days all of them were gathered, virgin samples were finally exposed and they were all developed in C-41 processing. Table 1 shows the speed values Sp.1 and Sp.2 of all samples respectively read at an optical density of 0.20 and 1.00 above fog.

TABLE 1

| | Sample S1 | | Sample S2 | | Sample S3 | | Sample S4 | |
|---|---|---|---|---|---|---|---|---|
| | Sp.1 | Sp.2 | Sp.1 | Sp.2 | Sp.1 | Sp.2 | Sp.1 | Sp.2 |
| Film 1 | 15.7 | 6.1 | 16.0 | 6.1 | 14.3 | 4.3 | 12.3 | 2.2 |
| Film 2 | 15.5 | 4.7 | 16.2 | 5.9 | 15.2 | 4.8 | 14.9 | 3.2 |
| Film 3 | 14.6 | 3.4 | 14.9 | 3.9 | 14.7 | 4.1 | 16.9 | 4.1 |
| Film 4 | 13.9 | 5.6 | 14.3 | 6.3 | 12.8 | 5.2 | 9.0 | 2.6 |

It is worth noting the gain in speed read at 0.20 above fog (Sp.1) of films 1, 2 and 3, containing compound 1 of the present invention in comparison with the same speed of film 4 which does not have compound 1 of the present invention.

EXAMPLE 2

A control multilayer negative color film (Film 5) was made by coating a subbed cellulose triacetate support with the following layers in the indicated order:

Layer 1: Antihalation gelatin layer containing 0.17 g/m$^2$ of black colloidal silver and 1.47 g/m$^2$ of gelatin;

Layer 2: Interlayer containing 0.64 g/m$^2$ of gelatin.

Layer 3: Slower red-sensitive, cyan dye forming, silver halide emulsion layer comprising a blend of a 60% (by weight) of a relatively slower AgBrI emulsion (having 97.5% moles Br$^-$, 2.5% moles I$^-$, an average grain size of 0.31 μm and a silver/gelatine ratio of 1.12), chemically ripened with gold and thiosulphate and of 40% (by weight) of a relatively faster AgBrICl emulsion (having 87.7% moles Br$^-$, 7.17% moles I$^-$, 5.13% moles Cl$^-$, an averase grain size of 0.43 μm, and a silver/gel ratio of 1.26), chemically ripened with gold and thiosulphate. The emulsion blend was stabilized with 4-methyl-6-hydroxy-tetraazaindene and added with red spectral sensitizer S-1 and red spectral sensitizer S-2.

The layer was coated at a total silver coverage of 1.27 g/m$^2$, 100.5 mg/m$^2$ of the magenta colored cyan dye forming coupler C-1, 522 mg/m$^2$ of the 4-equivalent cyan dye forming coupler C-2 and 1.65 g/m$^2$ of gelatin.

Layer 4: Faster red sensitive, cyan dye forming, silver halide emulsion layer comprising a fast silver bromoiodide emulsion (having 89% moles Br$^-$ and 11% moles I$^-$, an average grain size of 0.62 μm and a silver/gelatin ratio of 1.2), chemically ripened with gold and thiosulphate, stabilized with 4-methyl-6-hydroxy tetraazaindene and added with red spectral sensitizer S-1 and red spectral sensitizer S-2.

The layer was coated at a silver coverage of 0.82 g/m$^2$, 23.3 mg/m$^2$ of the magenta colored cyan dye forming coupler C-1, 35 mg/m$^2$ of the 4-eqivalent cyan dye forming coupler C-2, 35 mg/m$^2$ of the 2-equivalent cyan dye forming coupler C-3, 6.4 mg/m$^2$ of the cyan dye forming DIR coupler C-4 and 0.82 g/m$^2$ of gelatin.

Layer 5: Interlayer containing 1.05 g/m$^2$ of gelatin and 69 mg/m$^2$ of 2,5-tert.octylhydroquinone.

Layer 6: Slower green sensitive, magenta forming, silver halide emulsion layer comprising a blend of a 40% (by weight) of a relatively slower AgBrI emulsion (having 97.5% moles Br$^-$, 2.5% moles I$^-$, an average grain size of 0.31 μm and a silver/gelatin ratio of 1.12), chemically ripened with gold and thiosulphate and of 60% (by weight) of a relatively faster AgBrICl emulsion (having 87.7% moles Br$^-$, 7.17% moles I$^-$, 5.13% moles Cl$^-$, an average grain size of 0.43 μm, and a silver/gelatin ratio of 1.26), chemically ripened with gold and thiosulphate. The emulsion blend was stabilized with 4-methyl-6-hydroxy-tetraazaindene and added with green spectral sensitizer S-3 and green spectral sensitizer S-4.

The layer was coated at a total silver coverage of 1.52 g/m$^2$, 92 mg/m$^2$ of the yellow colored magenta dye forming coupler C-5, 46 mg/m$^2$ of the yellow colored magenta dye forming coupler C-6, 575 mg/m$^2$ of the 4-equivalent magenta dye forming coupler C-7, 60 mg/m$^2$ of the magenta forming DIR coupler C-8 and 1.65 g/m$^2$ of gelatin.

Layer 7: Faster green sensitive, magenta-dye forming, silver halide emulsion layer comprising a fast silver bromo-iodide emulsion (having 89% moles Br$^-$ and 11% moles I$^-$, an average grain size of 0.62 μm and a silver/gelatin ratio of 1.2), chemically ripened with gold and thiosulphate, stabilized with 4-methyl-6-hydroxy-tetraazaindene and added with green spectral sensitizer S-3 and green spectral sensitizer S-4. The layer was coated at a total silver coverage of 0.84 g/m$^2$, 16 mg/m$^2$ of the yellow colored magenta dye forming coupler C-5, 8 mg/m$^2$ of the yellow colored magenta dye forming coupler C-6, 137 mg/m$^2$ of the 4-equivalent magenta dye forming coupler C-7, 6.3 mg/m$^2$ of the magenta forming DIR coupler C-8 and 0.84 g/m$^2$ of gelatin.

Layer 8: Interlayer containing 0.79 g/m$^2$ of gelatin.

Layer 9: Yellow colloidal silver filter layer comprising 0.080 g/m$^2$ of silver, 1.22 g/m$^2$ of gelatin and 94 g/m$^2$ of 2.5-tert.-octylhydroquinone.

Layer 10: Slower blue-sensitive, yellow dye forming, silver halide emulsion layer comprising a blend of a 60% (by weight) of a relatively slower AgBrI emulsion (having 97.5% moles Br$^-$, 2.5% moles I$^-$, an average grain size of 0.31 μm and a silver/gelatin ratio of 1.12), chemically ripened with gold and thiosulphate and of 40% (by weight) of a relatively faster AgBrICl emulsion (having 87.7% moles Br$^-$, 7.17% moles I$^-$, 5.13% moles Cl$^-$, an average grain size of 0.43 μm and a silver/gelatin ratio of 1.26), chemically ripened with gold and sulfur. The emulsion blend was stabilized with 4-methyl-6-hydroxy-tetraazaindene and added with blue spectral sensitizer S-5 and 638 mg/mole Ag of 1,2-dihydro-6-hydroxy-2-oxo-4-pyridincarboxylic acid stabilizer (compound C).

The layer was coated at a total silver coverage of 0.83 g/m$^2$, 1529 mg/m$^2$ of the 2-equivalent yellow dye forming coupler C-9 and 1.73 g/m$^2$ of gelatine.

Layer 11: Faster blue sensitive, yellow-dye forming, silver halide emulsion layer comprising a fast silver bromoiodide emulsion (having 89% moles Br$^-$ and 11% moles I$^-$, an average grain size of 0.62 μm and a silver/gelatin ratio of 1.2), chemically ripened with gold and thiosulphate and added with 472 mg/mole Ag of 1,2-dihydro-6-hydroxy-2-oxo-4-pyridincarboxilic acid stabilizer.

The layer was coated at a total silver coverage of 0.38 g/m$^2$, 148 mg/m$^2$ of the 2-equivalent yellow dye forming coupler C-9, 6 mg/m$^2$ of the yellow dye forming DIR coupler C-10 and 0.90 g/m$^2$ of gelatin.

Layer 12: Interlayer containing 0.98 g/m$^2$ of gelatin and 131 mg/m$^2$ of the UV absorber D-1 and 131 mg/m$^2$ of the near UV absorber D-2.

Layer 13: Protective gelatin overcoat comprising 0.72 g/m$^2$ of gelatin and the hardener monochloro dihydroxy triazine.

A multilayer negative color film (Film 6) as a comparative test, was made by coating the subbed cellulose triacetate support with the layers from 1 to 9 exactly as the layers 1 to 9 of the control film (film 5) and then with the following layers:

Layer 10: Slower blue sensitive, yellow dye forming, silver halide emulsion layer comprising the same emulsion blend as the control film except that the 3-allylbenzothiazolium bromide compound (348 mg/mole Ag) was added instead of the blue spectral sensitizer S-5 and compound C.

The layer was coated at a total silver coverage of 0.83 g/m$^2$, 1529 mg/m$^2$ of the 2-equivalent yellow dye forming coupler C-9 and 1.73 g/m$^2$ of gelatin.

Layer 11: Faster blue sensitive, yellow-dye forming, silver halide emulsion layer comprising the same fast silver bromoiodide emulsion as the control film, except that the 3-allylbenzothiazolium bromide compound (208 mg/mole Ag) was added instead of compound C.

The layer was coated at a total silver coverage of 0.38 g/m$^2$, 148 mg/m$^2$ of the 2-equivalent yellow dye forming coupler C-9, 6 mg/m$^2$ of the yellow dye forming DIR coupler C-10 and 0.90 g/m$^2$ of gelatin.

Layers 12 and 13 were prepared and coated exactly in the same way as the control film (Film 5).

A multilayer negative color film (film 7) according to the present invention was made by coating the subbed cellulose triacetate support with the layers from 1 to 9 exactly as the layers 1 to 9 of the control film (film 5) and then with the following layers:

Layer 10: Slower blue sensitive, yellow dye forming, silver halide emulsion layer comprising the same emulsion blend as the control film except that compound 1 of the present invention (219 mg/mole Ag) was added instead of the spectral sensitizer S-5 and compound C. The layer was coated at a total silver coverage of 0.83 g/m$^2$, 1529 mg/m$^2$ of the 2-equivalent yellow dye forming coupler C-9 and 1.73 g/m$^2$ of gelatin.

Layer 11: Faster blue sensitive, yellow-dye forming, silver halide emulsion layer comprising the same fast silver bromoiodide emulsion as the control film, except that compound 1 of the present invention (131 mg/mole Ag) was added instead of compound C.

The layer was coated at a total silver coverage of 0.38 g/m$^2$, 148 mg/m$^2$ of the 2-equivalent yellow dye forming coupler C-9, 6 mg/m$^2$ of the yellow dye forming DIR coupler C-10 and 0.90 g/m$^2$ of gelatin.

Layers 12 and 13 were prepared and coated exactly in the same way as the control film (5).

Compounds used in the above film are the following:

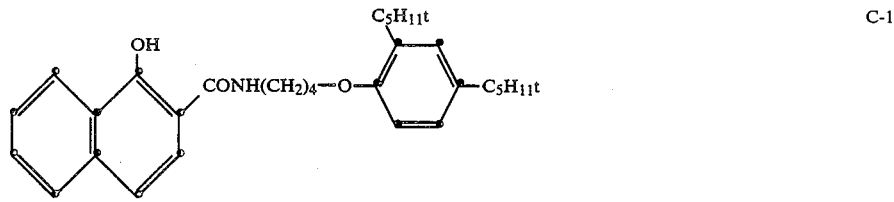

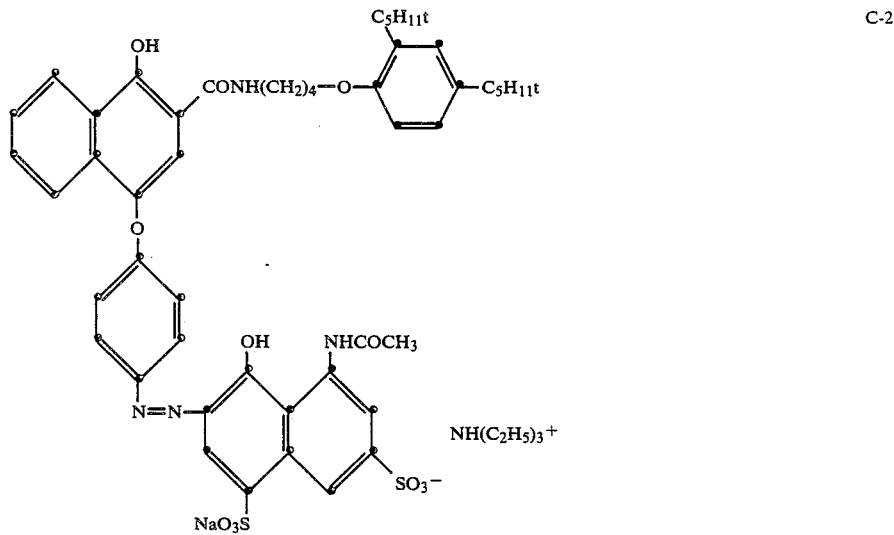

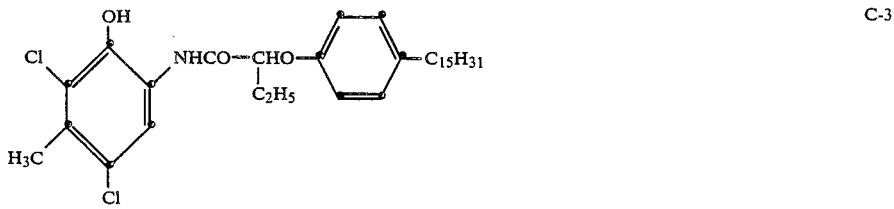

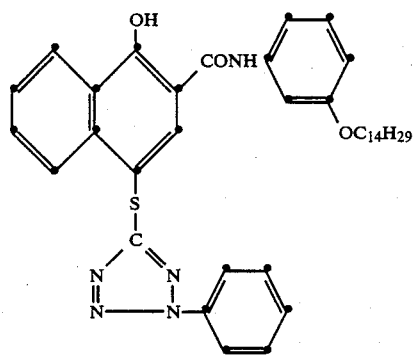
C-4
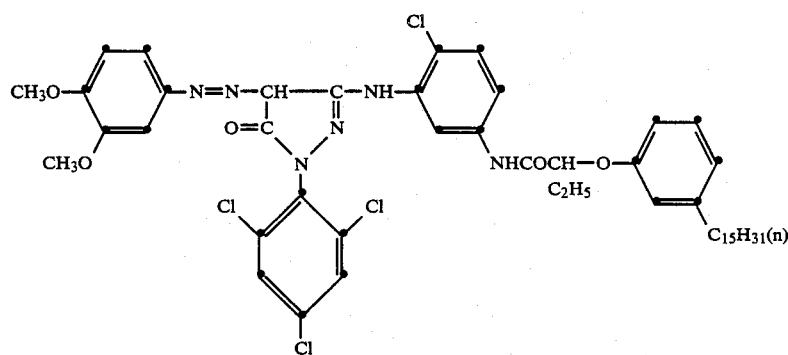
C-5
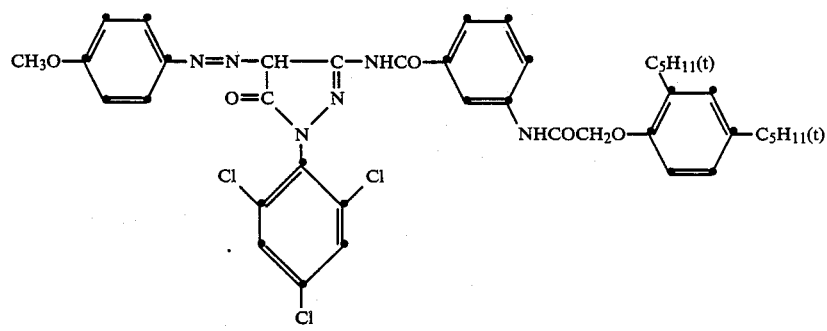
C-6
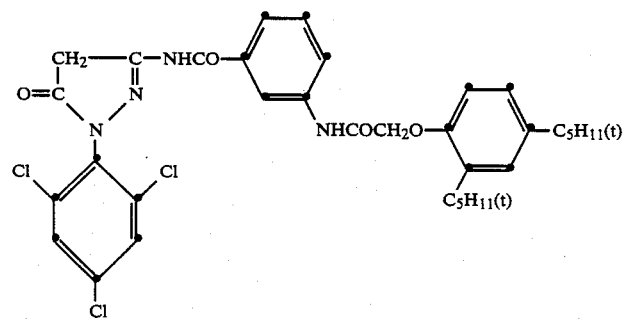
C-7

-continued
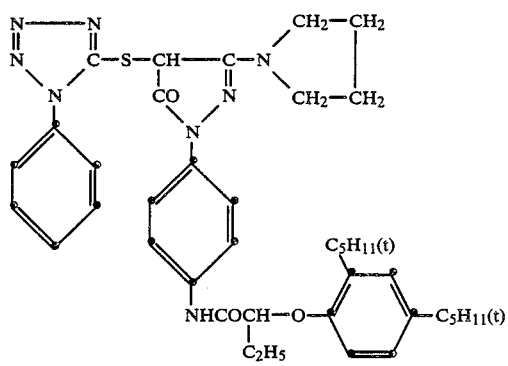
C-8
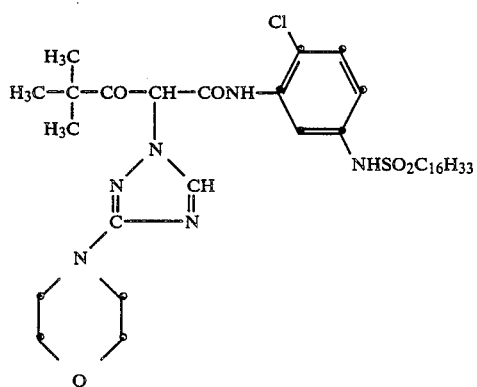
C-9
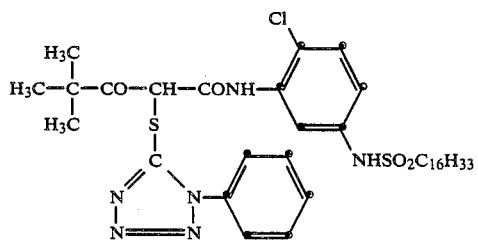
C-10
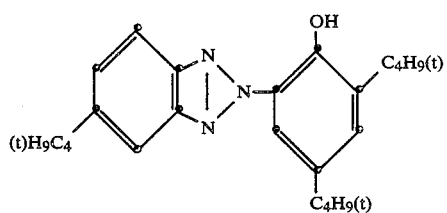
D-1
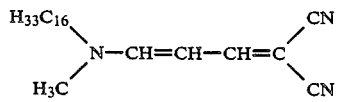
D-2
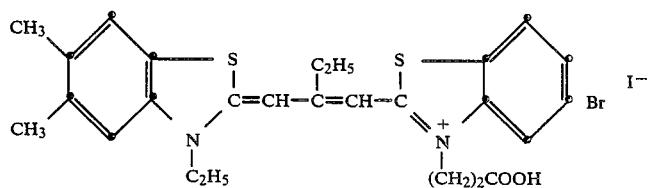
S-1

-continued

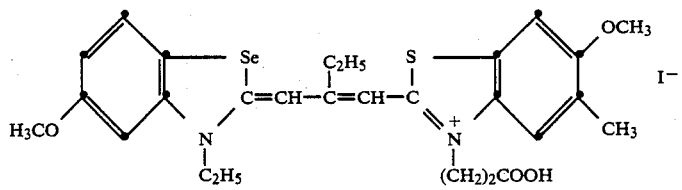
S-2

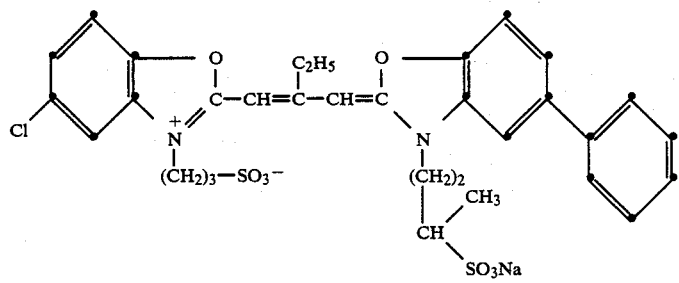
S-3

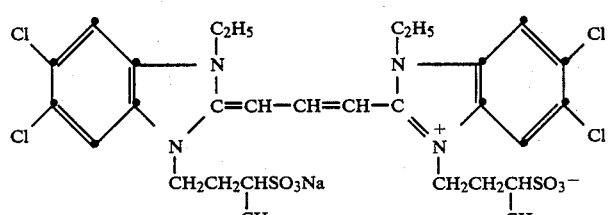
S-4

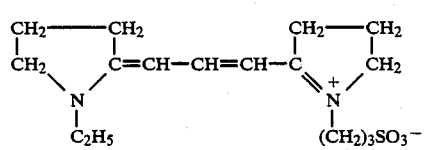
S-5

The films were aged 7 days at controlled temperature and humidity (24° C., 90% RH), keeping their references at shelf conditions.

The films were then exposed on a sensitometer through a continuous wedge at 5500° K. and processed using Kodak Flexicolor process which is described in the British Journal of Photography, July 12, 1974, pages 597 to 598.

The differences of photographic characteristics of the aged films vs. their respective shelf, relatively to yellow layer, are shown in Table II, hereinafter:

TABLE II

| FILM | TYPE | D.min | D.max |
|---|---|---|---|
| 5 | CONTROL | +0.02 | +0.30 |
| 6 | COMPARISON | +0.05 | +0.25 |
| 7 | INVENTION | 0.00 | +0.08 |

As illustrated in Table II, the film 7, containing compound 1 of the present invention, shows a reduced increase (undesired) of D.max of the yellow curve and no rise of D.min.

Furthermore, new samples of the same films were conditioned at 85% RH and room temperature, for a lapse of 3 days, then sealed vapor tight and placed in 50° C. room for 3 days.

The films were then processed as described above.

D.min increase of cyan, magenta and yellow layers of the conditioned films vs. shelf references is reported in Table III:

TABLE III

| FILM | TYPE | CYAN | MAGENTA | YELLOW |
|---|---|---|---|---|
| 5 | CONTROL | +0.16 | +0.15 | +0.36 |
| 6 | COMPARISON | +0.16 | +0.13 | +0.58 |
| 7 | INVENTION | +0.06 | +0.02 | +0.04 |

Surprisingly, compound 1 of the present invention, added to both yellow hemilayers of the film 7, controls the rise of fog of each light sensitive layers, occurring under the aforementioned incubation of the film samples.

I claim:

1. A silver halide light-sensitive material comprising a silver halide light-sensitive emulsion associated with a benzo-bis-thiazole quaternary salt antifogging agent having attached to at least one quaternary nitrogen thereof an alkenyl group having a double bond in β-position.

2. The silver halide light sensitive material of claim 1, wherein said benzo-bis-thiazole quaternary salt is represented by the general formula (I):

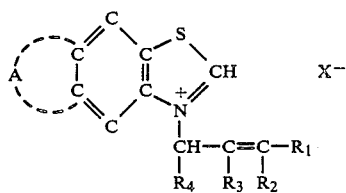

(I)

wherein $R_1$, $R_2$, $R_3$, $R_4$ each represents a hydrogen atom or a lower alkyl group, A is the atoms necessary to complete a benzo-bis-thiazole nucleus and $X^-$ is an anion.

3. The silver halide light-sensitive material of claim 1, wherein said benzo-bis-thiazole quaternary salt is represented by the general formula (II):

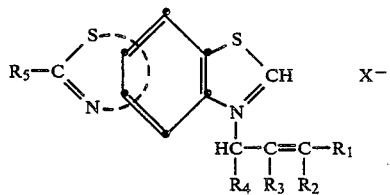

(II)

wherein $R_5$ represents a hydrogen atom or a lower alkyl group; $R_1$, $R_2$, $R_3$ and $R_4$ each represents a hydrogen atom or a lower alkyl group and $X^-$ is an anion.

4. The silver halide light-sensitive material of claim 3, wherein said lower alkyl group is a methyl group, an ethyl group, a propyl group, an iso-propyl group, a butyl group, an iso-butyl group or a tertiary-butyl group, a normal pentyl group or a tert.-amyl group.

5. The silver halide light-sensitive material of claim 1, wherein said benzo-bis-thiazole quaternary salt is a chloride, bromide or iodide salt.

6. The silver halide light-sensitive material of claim 1, wherein said antifogging agent is one of the following compounds:

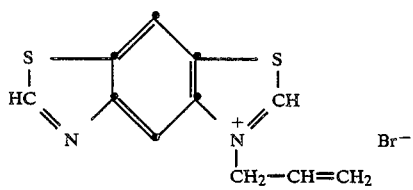

(1)

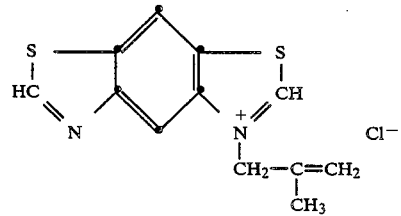

(2)

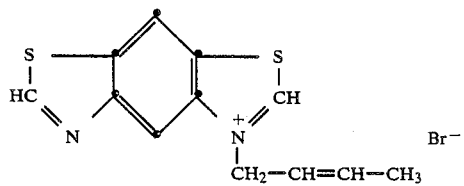

(3)

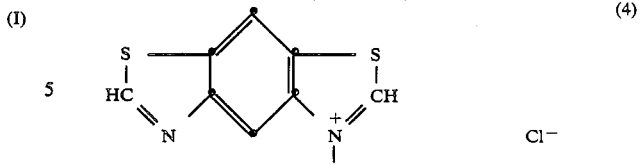

(4)

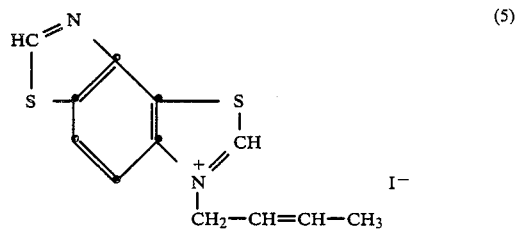

(5)

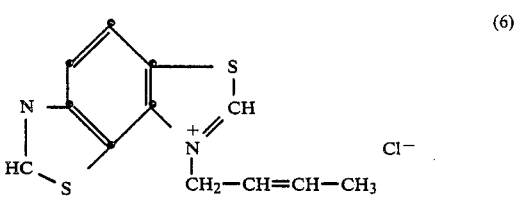

(6)

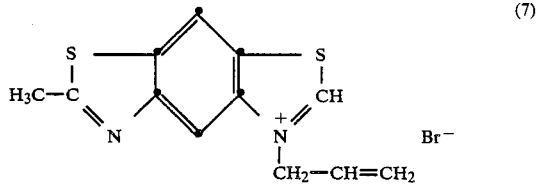

(7)

7. The silver halide light-sensitive material of claim 1, wherein said silver halide is silver chloride, silver bromide, silver bromo-chloride, silver iodo-bromide or silver iodo-bromo-chloride.

8. The silver halide light-sensitive material of claim 1, wherein said silver halide light-sensitive emulsion has been chemically sensitized.

9. The silver halide light-sensitive material of claim 1, wherein said silver halide light-sensitive emulsion has been optically sensitized.

10. The silver halide light-sensitive material of claim 1, wherein said silver halide light-sensitive emulsion is associated with a dye-forming coupler.

11. A silver halide light-sensitive material comprising a support base carrying at least one silver halide blue-sensitive emulsion layer, associated with a yellow dye forming coupler, at least one silver halide green-sensitive emulsion layer, associated with a magenta dye forming coupler and at least one red-sensitive silver halide emulsion layer, associated with a cyan dye forming coupler, wherein at least one of said silver halide emulsion layers is associated with an antifogging agent of claim 1.

12. Benzo-bis-thiazole quaternary salts corresponding to the general formula (I):

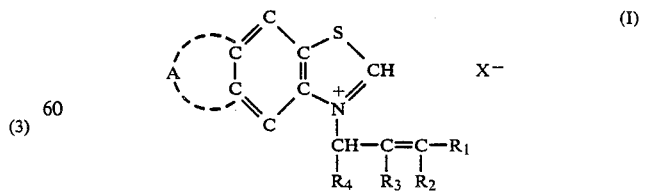

(I)

wherein $R_1$, $R_2$, $R_3$, $R_4$ each represents a hydrogen atom or a low alkyl group, A represents the atoms necessary to complete a benzo-bis-thiazole nucleus and $X^-$ represents an anion.

* * * * *